United States Patent [19]
Peterson

[11] Patent Number: 5,380,280
[45] Date of Patent: Jan. 10, 1995

[54] ASPIRATION SYSTEM HAVING PRESSURE-CONTROLLED AND FLOW-CONTROLLED MODES

[76] Inventor: Erik W. Peterson, 1860 Newell Ave., Walnut Creek, Calif. 94595

[21] Appl. No.: 150,715

[22] Filed: Nov. 12, 1993

[51] Int. Cl.⁶ .................. A61M 31/00; A61M 1/00; A61M 5/00
[52] U.S. Cl. ...................... 604/65; 604/119; 604/246
[58] Field of Search .......... 604/31, 35, 65–67, 604/118, 119, 73, 246, 317–320

[56] References Cited

U.S. PATENT DOCUMENTS

| | | | |
|---|---|---|---|
| 4,706,687 | 11/1987 | Rogers et al. | 604/65 |
| 4,740,202 | 4/1988 | Stacey et al. | 604/119 |
| 4,886,498 | 12/1989 | Newton | 604/65 |
| 4,930,997 | 6/1990 | Bennet | 604/319 |
| 4,973,311 | 11/1990 | Iwakoshi et al. | 604/119 |
| 5,098,387 | 3/1992 | Wiest et al. | 604/67 |
| 5,178,606 | 1/1993 | Ognier et al. | 604/67 |
| 5,242,404 | 9/1993 | Conley et al. | 604/67 |

Primary Examiner—C. Fred Rosenbaum
Assistant Examiner—Frank Wilkens, III
Attorney, Agent, or Firm—Godfrey & Kahn

[57] ABSTRACT

An aspiration system (10) having pressure-controlled and flow-controlled modes comprises connective plumbing (26), a collector (14), a pump (12), a variable flow resistor (20), a pressure sensor (18), and a control circuit (24). The connective plumbing (26) includes a conduit (28) which communicates with the surgical site from which fluid is to be aspirated and delivered to the collector (14). The pump (12) induces flow from the surgical site to the collector (14). The variable flow resistor (20) and the pressure sensor (18) are in fluid communication with the conduit (28) by the connective plumbing (26). In the pressure-controlled mode, the variable flow resistor (26) is adjusted to maintain a preselected pressure according to an output signal (50) from the pressure sensor (18). In the flow controlled mode, the pump (12) is adjusted to maintain a preselected flow according to a pressure differential in the connective plumbing across the variable flow resistor (20). The system (10) further includes a gas source (22) which is inputted into the variable flow resistor (20) to provide a known pressure against which the pressure in the remainder of the connective plumbing is compared to establish the pressure differential. The connective plumbing (26) further includes a flow director (16) permitting flow only in one direction to avoid contamination of certain portions of the connective plumbing (26). The contaminated portions of the connective plumbing (26) are discarded.

12 Claims, 7 Drawing Sheets

ASPIRATION SYSTEM HAVING PRESSURE-CONTROLLED AND FLOW-CONTROLLED MODES

FIELD OF THE INVENTION

The present invention relates to devices used to aspirate fluids from a patient during surgery, and more specifically to an apparatus which includes both pressure controlled and flow controlled modes.

BACKGROUND OF THE INVENTION

In surgery, and particularly in ophthalmic surgery, there are many applications for aspiration systems which provide an aspiration level responsive to some surgeon-operated control, such as a footpedal. Such aspiration systems may be classified as either pressure-controlled or flow-controlled, depending upon whether it is the pressure (vacuum) level or the flow level which is directly responsive to the surgeon's input. Within the scope of ophthalmic surgery, pressure-controlled aspiration systems have proven to be advantageous for most aspects of vitreoretinal surgery and flow-controlled aspiration systems have proven to be advantageous for most aspects of cataract surgery. Since both types of surgery may be performed in a given medical facility, there is a need for an aspiration system capable of operating in either a pressure-controlled or a flow-controlled mode.

With specific regard to pressure-controlled aspiration systems, the present standard for pressure-controlled aspiration is the venturi system, which is powered by compressed gas at a high flow rate. This requires an external compressor or tank of compressed gas, which limits the portability of the overall system. Accordingly, there is a need for a more portable aspiration system with performance comparable to the best pressure-controlled aspiration systems at a lower power requirement.

Pressure-controlled aspiration systems of the venturi type routinely provide a means of sensing the actual pressure (vacuum) level being delivered without contamination of the non-disposable parts of the system by fluids aspirated from the surgical site. However, peristaltic aspiration systems, which are the present standard for flow-controlled systems, typically must allow aspirated fluid to come in contact with the pressure sensor. Various means, such as filtration to remove bacteria and flushing with clean liquid at the conclusion of the surgery, have been tried to minimize the safety and reliability issues raised by this contamination. There is, however, a need for a better solution to this problem, particularly in view of current concerns over diseases transmitted by viruses, which cannot easily be removed by filtration.

SUMMARY OF THE INVENTION

In accordance with the present invention, the aspiration system having pressure-controlled and flow-controlled modes of the present invention comprises connective plumbing, a collector, a pump, a variable flow resistor, a pressure sensor, and control means. The connective plumbing includes a conduit which communicates with the surgical site from which fluid is to be aspirated. The collector includes a collection bag which receives aspirated fluid from the conduit. The pump is preferably of the peristaltic type, and induces flow of aspirated fluid from the conduit to the collector. The variable flow resistor includes a proportional valve which is disposed in fluid communication with the connective plumbing, the pump, and the collector. The pressure sensor is likewise in communication with the collector, the pump, and the variable flow resistor.

The control means is a circuit which receives an output signal from the pressure sensor and which further controls the variable flow resistor, and the aspiration system in two different modes of operation. In the first mode, the pressure of fluid conveyed by the conduit is controlled; and in the second mode the flow of fluid conveyed by the conduit is controlled. In the first mode, the variable flow resistor is adjusted to maintain a pre-selected pressure according to the output signal from the pressure sensor. In the second mode, the variable flow resistor is adjusted to maintain a pre-selected flow according to a pressure differential in the connective plumbing across the variable flow resistor. The aspiration system further includes a gas source which is inputted into the variable flow resistor to provide a known pressure against which the pressure in the remainder of the connective plumbing is compared to establish the pressure differential.

The connective plumbing includes a first section and a second section separated by a flow director, the first section being in fluid communication with the conduit, the pump, and the collector, and the second section being in fluid communication with the pressure sensor, the variable flow resistor, and the gas source. The flow director permits flow only in the direction from the second section to the first section. The connective plumbing of the first section is disposable after a single patient use.

The present invention also provides as noted earlier an aspiration system capable of operating in either a pressure-controlled or flow-controlled mode. The present invention further provides a more conveniently portable aspiration system with performance comparable to the best pressure-controlled systems at a lower power requirement. Further, the present invention provides connective plumbing which is separable, the portion being in contact with aspirated fluid being disposable to avoid contamination.

Further objects, features, and advantages of the present invention will be apparent from the following detailed description taken in conjunction with the accompanying drawings.

Figure 1:
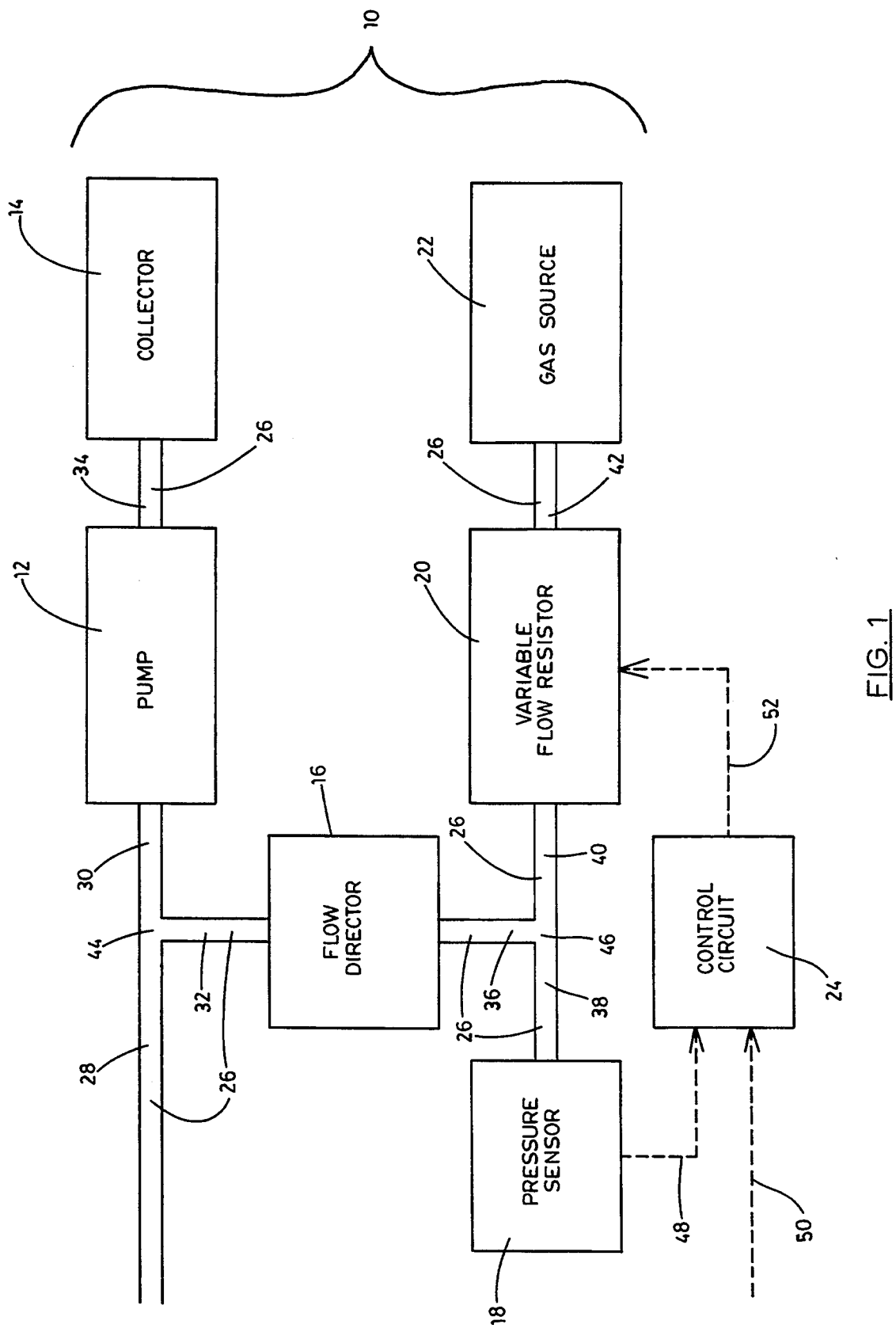
FIG. 1 is a block diagram of the aspiration system of the present invention and which has pressure-controlled and flow-controlled modes.

DESCRIPTION OF THE PREFERRED EMBODIMENT with reference to the drawings, the aspiration system having pressure-controlled and flow-controlled modes of the present invention is shown generally in FIG. 1 at the numeral 10. The aspiration system 10 generally includes a pump 12; a collector 14; a flow director 16; a pressure sensor 18; a variable flow resistor 20; a gas source 22; a control circuit 24; and connective plumbing 26.

The connective plumbing 26 includes conduits 28; 30; 32; 34; 36; 38; 40; and 42. The conduits 28, 30 and 32 are in fluid communication and meet to form juncture point 44. The conduit 28 is disposed in fluid communication with a surgical handpiece (not shown) and is operable to convey aspirated fluid from the surgical site to the juncture point 44. The conduit 30 conveys fluid from the juncture point 44 to the pump 12. The conduit 32 conveys fluid from the flow director 16 to the juncture point 44. The conduit 34 conveys fluid from the pump 12 to the collector 14. The conduits 36, 38, and 40 are connected in fluid communication and meet to form a juncture point 46. The conduit 36 conveys fluid from the juncture point 46 to the flow director 16. The conduit 38 conveys fluid from the juncture point 46 to the pressure sensor 18. The conduit 40 conveys fluid from the variable flow resistor 20 to the juncture point 46, and the conduit 42 maintains fluid communication between the variable flow resistor 20 and the gas source 22.

FIG. 1 further shows a wire connection or electrical pathway at 48 which conveys a signal from the pressure sensor 18 to the control circuit 24; a wire connection or electrical pathway at 50 which inputs a signal which constitutes the vacuum setpoint or maximum vacuum limits; and a wire connection or electrical pathway at 52 which sends an output signal from the control circuit 24 to the variable flow resistor 20.

Figure 2:
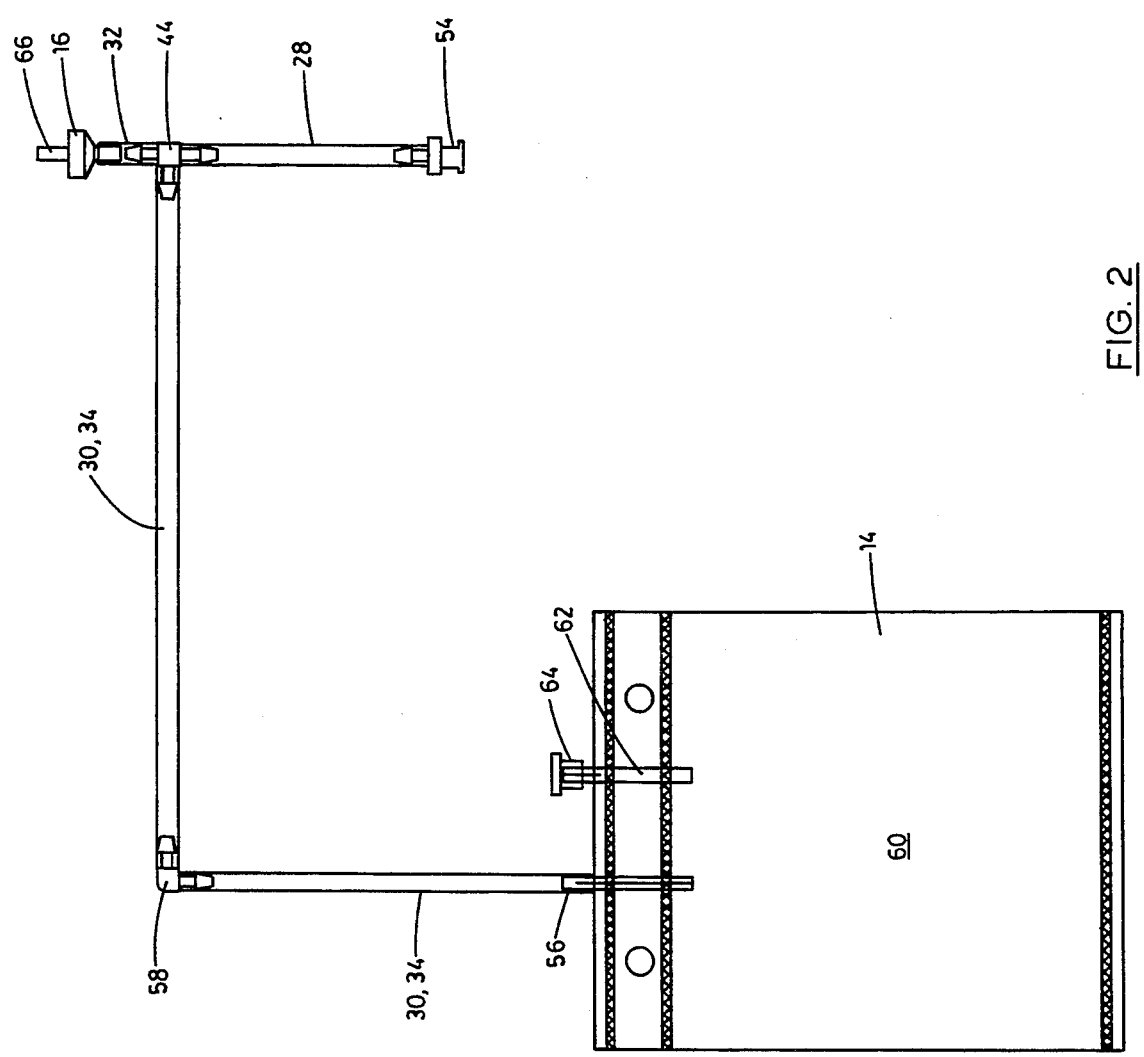
FIG. 2 is a plan view of the collector; the flow director; and portions of the connective plumbing of the aspiration system of the present invention.

FIG. 2 illustrates the conduits 28; 30; 32; and 34; the collector 14, and the flow director 16. These parts are intended to be disposed of after a single patient use. The conduit 28 is manufactured of flexible tubing which is connected at one end to the juncture point 44 and which terminates at its opposite end at a connector fitting 54. The conduit 28 may be further extended by connection of additional tubing to the connector fitting 54 or the connector fitting 54 may be directly attached to the surgical handpiece (not shown). The conduits 30 and 34 are collectively formed of a thick-walled flexible tubing intended for use with a peristaltic pump. They are connected at one end to the juncture point 44 and at the other end to an elbow fitting 58, and further extends between the elbow fitting 58 and at the other end to a tube fitting 56. The portion of conduit 34 which extends between the fittings 56 and 58 is preferably manufactured from tubing which is clear or transparent such that movement of aspirated material through the conduit 34 may be observed by a surgeon. The tube fitting 56 is sealed on the collector 14. As should be understood, the elbow fitting 58 facilitates the routing of the peristaltic tubing when the aspiration system 10 is assembled and made ready for operation, as will be explained below. The pump 12 is interposed to act upon the peristaltic tubing between juncture 44 and the elbow fitting 58 in a manner as also explained below, such that the peristaltic tubing between the juncture 44 and the pump 12 forms the conduit 30; and the peristaltic tubing between the pump 12 and the elbow fitting 58, together with the clear tubing between the elbow fitting 58 and the tube fitting 56, forms the conduit 34.

As seen in FIG. 2, the collector 14 includes a collection bag 60; a tube fitting 62; and a hydrophobic filter 64. The hydrophobic filter 64 acts to retain aspirated liquids and solid material within the collection bag 60, yet vents the collection bag 60 to the atmosphere by permitting the escape of air entrapped within the collection bag. The conduit 32 is manufactured of tubing connected at one end to the juncture point 44 and at the other end to an outlet of the flow director 16. The juncture point 44 is formed of a standard "T" fitting. As shown in FIG. 2, the flow director 16 is preferably a one-way or check valve, but other flow directing means such as a hydrophobic filter may be employed in place of same. An inlet of the flow director 16 terminates in a male connector fitting 66 which may be removably connected to the conduit 36.

Figure 3:
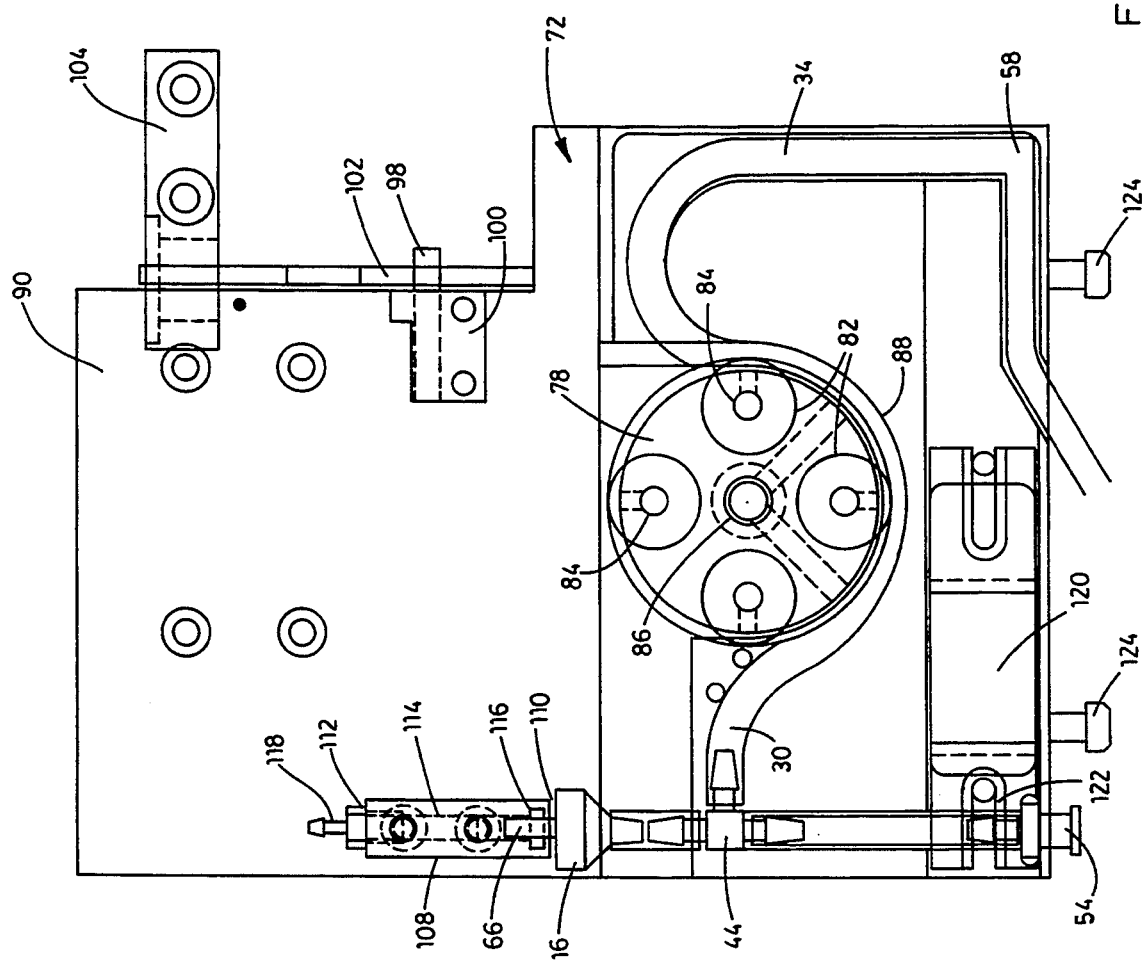
FIG. 3 is a fragmentary, plan view of the pump utilized with the aspiration system of the present invention with the stepping motor removed.
Figure 4:
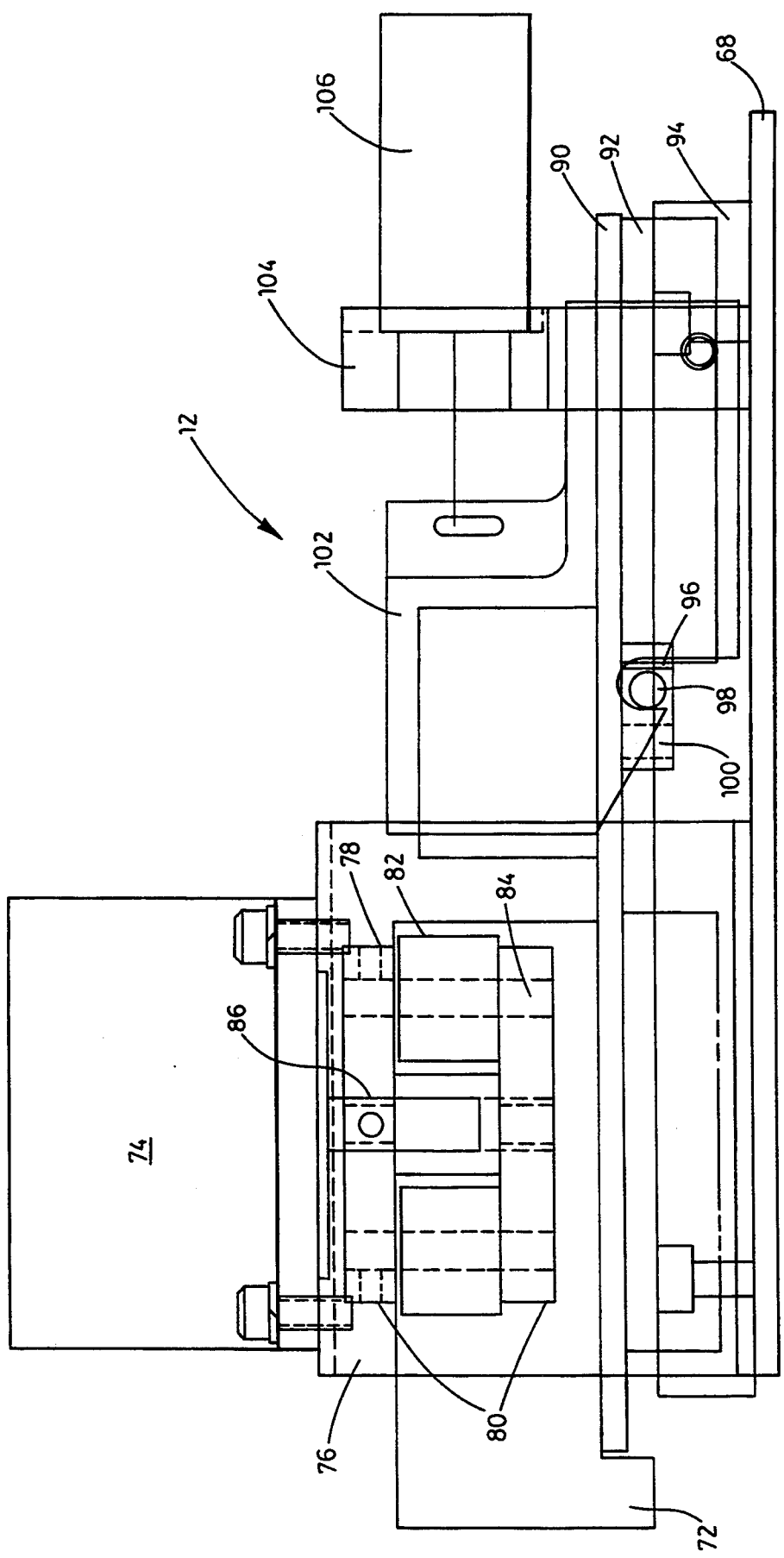
FIG. 4 is a fragmentary side elevation view of the pump utilized with the aspiration system of the present invention.
Figure 5:
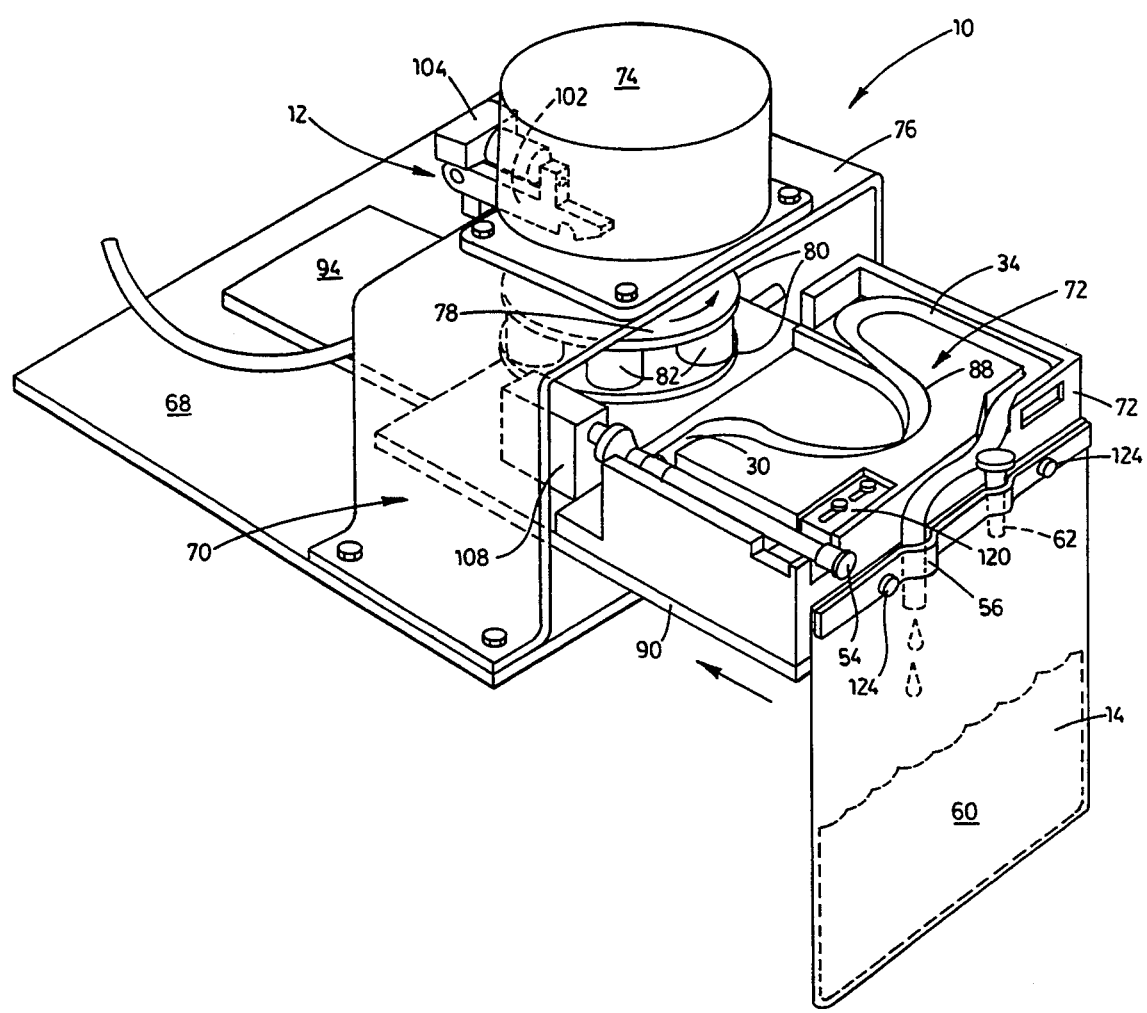
FIG. 5 is a perspective view of the pump utilized with the aspiration system of the present invention, with the associated drawer withdrawn.

FIGS. 3, 4, and 5 show various views of the pump 12 of the aspiration system 10. The pump 12 is preferably of the peristaltic type. The pump includes a base 68; a fixed assembly 70; and a drawer 72. The fixed assembly 70 includes a stepping motor 74; a stepping motor mounting bracket 76; and a rotatable hub 78. The stepping motor 74 is mounted upon the stepping motor mounting bracket 76; and the stepping motor mounting bracket 76 is mounted upon the base 68. The rotatable hub 78 includes two disks 80 and four rollers 82. The rollers 82 are arranged in a cross-like pattern about the periphery of the hub 78 and are individually positioned or sandwiched between the disks 80. It is to be understood that there may be other arrangements and numbers of the rollers 82. The rollers 82 are each rotatably attached to the disks 80 by concentric, axially directed pins 84. The rotatable hub 78 is attached about its axis to a drive shaft 86 of the stepping motor 74. The drive shaft 86 extends through an aperture (not shown) in the stepping motor mounting bracket 76. As shown by the arrow in FIG. 5, the stepping motor 74 rotates the hub 78 in a predetermined direction.

The drawer 72 is movable along a predetermined path of travel relative to the stepping motor 74; the hub 78; and the remainder of the fixed assembly 70. FIGS. 3 and 4 show the drawer 72 inserted into a position ready for operation of the pump 12; while FIG. 5 shows the drawer 72 withdrawn from the remainder of the pump 12. The drawer 72 includes a curved backplate which is shaped to substantially conform to the hub 78. Further, the tubing which forms the conduits 30 and 34 is routed or otherwise disposed about the rollers 82 and is thereafter compressed or sandwiched between the rollers 82 and the backplate 88 when the drawer 72 is inserted in a position ready for operation of the pump 12 (FIG. 4). As the stepping motor 74 is energized the hub 78 rotates in a predetermined direction. When this occurs, the rollers 82 engage the tubing which forms the conduits 30 and 34. This action occludes the tubing at the point where it is compressed between one of the rollers 82 and the backplate 88. As this point of occlusion moves, fluid is drawn through the tubing.

The drawer 72 is attached by means of a plate 90 to a slide mechanism 92. The slide mechanism 92 is moveable along a track 94 which is attached to the base 68. The movement of the drawer 72 by means of the slide mechanism 92 is substantially linear. When the drawer 72 is withdrawn, the tubing which forms the conduits 30 and 34 may be released to make the disposable portion of the aspiration system 10 (the collector 14, the flow director 16, and the conduits 30, 32 and 34) accessible for removal or installation. The drawer 72 is normally retained in the position shown in FIG. 3 by a latch mechanism 96 which includes a pin 98, and a bracket 100 which are attached to the drawer 72 by means of the plate 90. The latch further includes a pawl 102 and a bracket 104 which are attached to the base 68. The pawl 102 engages the pin 98 in order to retain the drawer 72 in the position shown in FIG. 3. To withdraw the drawer 72, a solenoid 106 which is connected to the aforedescribed latch mechanism 96, may be electrically activated to disengage the pawl 102 from the pin 98.

FIGS. 3 and 5 further show an interface block 108 which enables fluid communication between the flow director 16 and the conduit 36. The interface block 108 has a first end 110; an opposing second end 112; and a passageway 114 which is bored therethrough between the first end 110, and the second end 112. The interface block further includes an O-ring seal 116 at the first end which is compressed between the male connector fitting 66 and the passageway 114 to form a leak-tight seal. The second end 112 of the interface block 108 terminates in a barb-shaped fitting 118. A passageway 114 is disposed in fluid communication with the barb-shaped fitting 118. The barb fitting 118 facilitates the connection of the conduit 36 such that other portions of the aspiration system 10 not shown in FIGS. 3, 4, and 5 may be connected thereto.

FIGS. 3 and 5 further show a locking mechanism 120 by which the connector fitting 54 may be prevented from rotating. The locking mechanism 120 receives the connector fitting 54 in a mating pocket 122 formed in the drawer 72. The locking mechanism 120 may be slid to the right (according to the orientation of FIG. 3) in order to permit removal of the connector fitting 54 from the drawer 72.

As shown in FIG. 5, the collector 14, is attached to the drawer 72. The attachment of the collector 14 is accomplished by pins 124, which are viewable in FIG. 3. As best seen in FIG. 5, the collector bag 60 is suspended from the drawer 72 and the tube fitting 56 is connected to the conduit 34.

Figure 6:
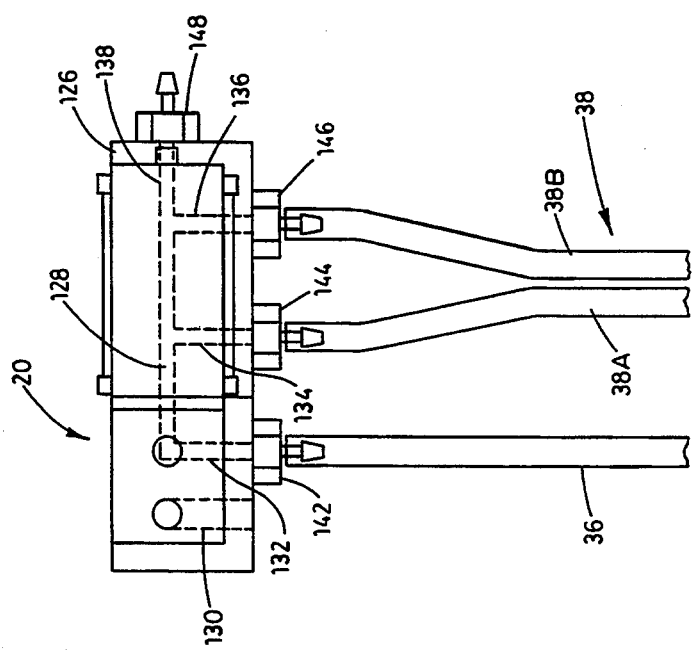
FIG. 6 is a top plan view of the variable flow resistor utilized with the aspiration system of the present invention, and shown with the internal passageways in phantom lines.
Figure 7:
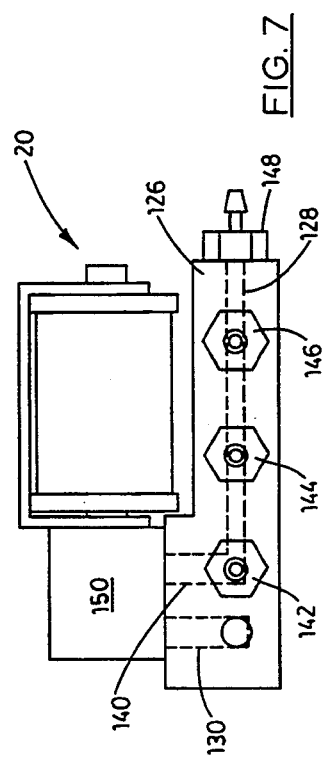
FIG. 7 is a side elevation view of the variable flow resistor of the aspiration system of the present invention, with the internal passageways being illustrated in phantom lines.

FIGS. 6 and 7 show in greater detail the preferred embodiment of the variable flow resistor 20. The variable flow resistor 20 includes a manifold block 126 having passageways 128, and 130, respectively. The passageway 128 includes a first branch 132; a second branch 134; a third branch 136; a fourth branch 138; and a fifth branch 140, all of which are disposed in fluid communication, one with the other. The first branch 132 of the passageway 128 terminates in a barb-shaped fitting 142, the second branch 134 of the passageway 128 terminates in a barb-shaped fitting 144; the third branch 136 of the passageway 128 terminates in a barb-shaped fitting 146; and the fourth branch 138 of the passageway 128 terminates in an orifice fitting 148. The conduit 36 is connected at one end to the barb fitting 118 (best viewed in FIG. 3) and is connected at its opposite end to the barb-shaped fitting 142. This places conduit 36 in fluid communication with the first branch 132 of the passageway 128. As should be understood, the conduit 38 is actually a double conduit 38A and 38B and is connected to the juncture 46 at one end and is in fluid communication with the pressure sensor 18. Further, the conduit 38A is connected at its other end to the barb fitting 144; and the conduit 38B is connected at its other end to the barb fitting 146. In this arrangement, the conduit 38A is disposed in fluid communication with the second branch 134 and conduit 38B is disposed in fluid communication with the third branch 136. As noted above, the conduit 38 is a double conduit since the pressure sensor 18 is manufactured with two redundant pressure transducers which reduces the potential hazard to the patient from a failure of one of the pressure transducers.

The variable flow resistor 20 includes a fixed flow resistance through the orifice fitting 148, in parallel with a variable flow resistance formed by a proportional solenoid valve 150. The fifth branch 140 of the passageway 128 is connected to the first port of the solenoid valve 150. The fixed flow resistance through the orifice fitting 148 facilitates the maintenance of a small flow of gas required for the flow-controlled mode of operation of the aspiration system 10 of the present invention, described below. The conduit 40 therefore includes the portions of the passageway 128 which communicate with the orifice fitting 148 and with the first port of the proportional solenoid valve 150. The passageway 130 of the manifold block 126 communicates between the second port of the proportional solenoid valve 150 and the ambient atmosphere. The conduit 42 includes the passageway 130 and also the outlet from the orifice fitting 148. As should be understood, the gas source 22 in this instance is the ambient atmosphere. It is to be further understood that it would be possible to add a hose barb fitting (not shown) to the end of the passageway 130 in order to communicate with some other gas source. In this situation, where another gas source is employed, the barb fitting added to the end of the passageway 130 and the existing orifice fitting 148 would be connected to this additional gas source. An example of an alternate gas source includes a reservoir of air maintained by some other control means at a pressure approximately equal to the pressure at the surgical site. In ophthalmic surgery, this is typically 20 to 40 mm Hg above atmospheric pressure. This permits the differential pressure between the surgical site and the conduit 28 to be regulated all the way to zero.

Figure 8:
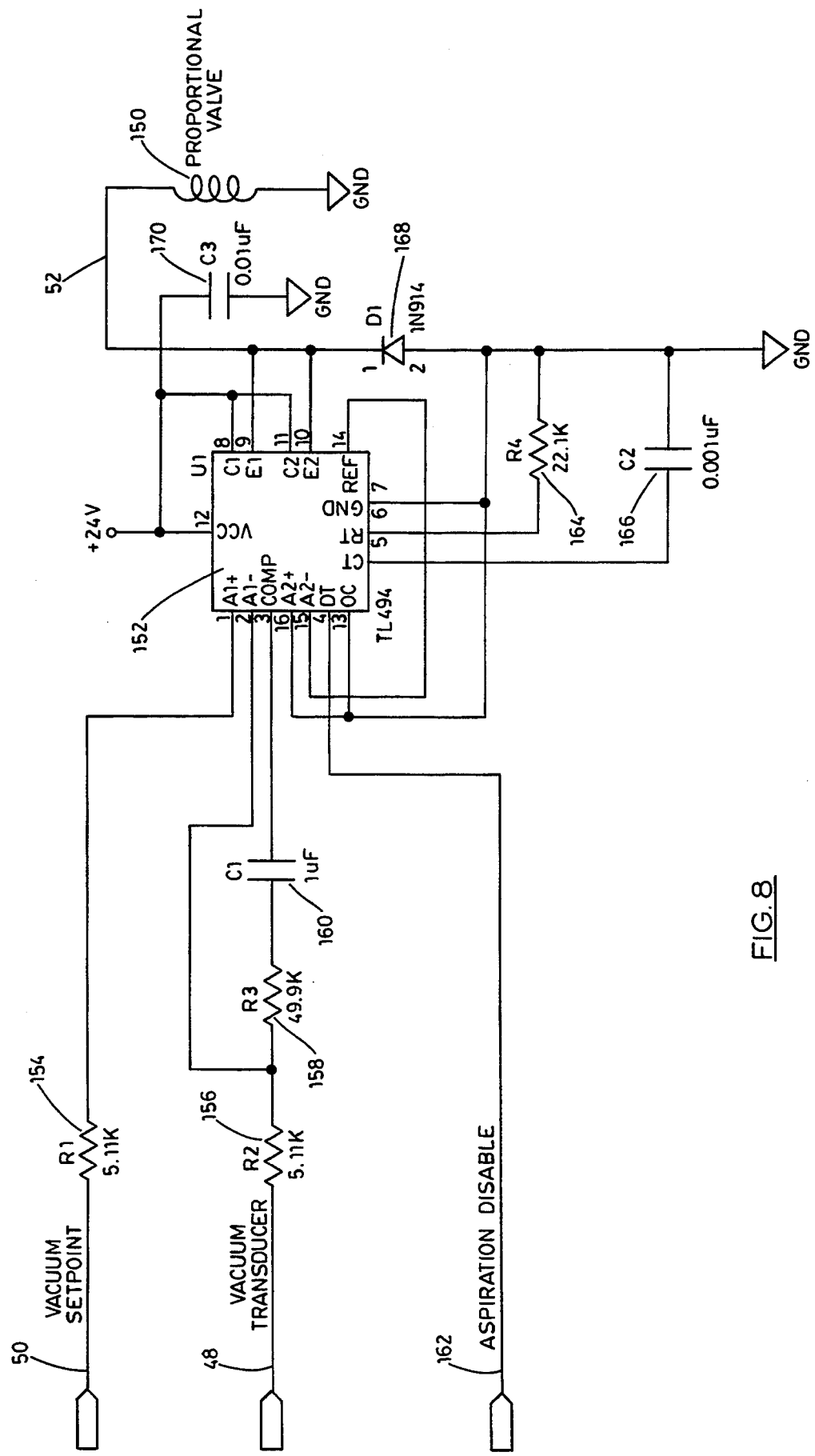
FIG. 8 is a schematic diagram of the control circuit [of] employed with the aspiration system of the present invention.

FIG. 8 illustrates in greater detail the preferred embodiment of the control circuit 24. The control circuit 24 includes an integrated circuit 152 (TL494) which is a pulse width modulation circuit designed primarily for use in switching power supplies. In this case, the pulse width modulated output at 52 is also suitable for driving the inductive load of the proportional valve solenoid 150. The degree of opening of the solenoid valve 150 is proportional to the average current through the solenoid 150, which is in turn proportional to the duty cycle of the pulse width modulated signal at 52. The integrated circuit 152 contains all of the active circuitry needed for closed loop control. As should be understood, the setpoint signal at 50 is applied at pin 1 of the integrated circuit 152, which is the non-inverting input of an operational amplifier. A resistor 154 which is used to compensate for input bias current is an optional feature. The feedback signal at 48 is applied through resistor 156 to pin 2 of the integrated circuit 152. The pin 2 is the inverting input of the operational amplifier. The output of the operational amplifier at pin 3 of the integrated circuit 152 is also fed back to pin 2 of the integrated circuit 152 through a resistor 158 and a capacitor 160. The exact values of the resistor 156, the resistor 158, and the capacitor 160 determine the open-loop gain and phase of the control system, and therefore the stability of the closed-loop system. Pin 3 of the integrated circuit 152 is also connected internally to control the pulse width modulation circuitry. Accordingly, increasing the voltage at pin 3 results in a decreasing duty cycle of the signal at 52. The pulse width modulation circuitry is also affected by an aspiration disable signal carried at 162 and applied at pin 4 of the integrated circuit 152. This controls the maximum duty cycle. For example, a voltage greater than a set amount, here 3.5 volts, sets the maximum duty cycle to zero, thereby effectively disabling the control system. To enable the control system, the signal carried at 162 should be near ground potential. Further, a resistor 164 and a capacitor 166 determine the frequency of the pulse width modulated output at 52. Additionally, a diode 168 clamps the signal carried at 52 near ground when the internal drive transistors of the integrated circuits 152 are deenergized. A capacitor 170 bypasses switching currents to reduce the coupling to other circuits through the power supply.

Operation

The operation of the described embodiment of the present invention is believed to be readily apparent and is briefly summarized at this point.

In the operation of the aspiration system 10, the drawer 72 is withdrawn by activation of the solenoid 106. The conduits 28, 30, 32, and 34, the collector 14, and the flow director 16 are installed into the pump 12, these parts being disposable as discussed earlier after a single use. The connector fitting 54 is then locked into place by the locking mechanism 120. The conduits 30, and 34 are routed about the rotatable hub 78 and the remaining connective plumbing is generally laid out as indicated in FIG. 3. The collector bag 60 is hung from the pins 124, and the drawer 72 is "closed" or inserted into the pump 12. When the drawer 72 is inserted into the pump 12, the conduits 30, and 34 are compressed between the rollers 82 and the backplate 88. As described above, the activation of the stepping motor 74 causes the hub 78 to rotate in a predetermined direction along the tubing which forms the conduits 30 and 34. When this occurs, fluid is drawn through the tubing.

The pump 12 induces a flow through the conduits 30 and 34 which is approximately independent of the pressure (vacuum) levels in the conduits 30 and 34. This flow is directed from the conduit 30 to the conduit 34 and is normally greater in magnitude than the flow into the conduit 28 from the surgical site. Thus, there normally is a flow through the conduit 32, which is directed into the conduit 30, and which is equal to the excess of the flow through the conduit 30 into the pump 12 and further above the flow into the conduit 28 from the surgical site. This flow includes gas originating from the gas source 22 and flowing through the conduit 42; the variable flow resistor 20; the conduits 40, and 36, and the flow director 16. The flow director 16 permits this flow, as long as it is directed from the conduit 36 into the conduit 32. As should be understood, the pressure differential between the conduit 40, and the conduit 42 depends upon the magnitude of the flow and the degree of restriction of the variable flow resistor 20. Since the pressure in the conduit 42 is maintained at a more or less constant level by the gas source 22, the pressure (vacuum) level in the conduit 40 can be controlled by the variable flow resistor 20. As should be understood, the pressure (vacuum) level in the conduits 28, 30, 32, 36, 38, and 40 are all approximately equal, so long as the flow resistance of the flow director 16 is negligible. The pressure (vacuum) level applied to the surgical handpiece through the conduit 28, therefore, can be controlled by the variable flow resistor 20. The control circuit 24 subsequently acts upon the variable flow resistor 20 to maintain this pressure (vacuum), as sensed by the pressure (vacuum) sensor 18, at the level set by the signal carried at 50.

When the aspiration system 10 is operated in a pressure-controlled mode, the pump 12 must be operated at a relatively high flow rate which exceeds the maximum expected flow from the surgical site through the conduit 28. The aspiration system 10 is then able to operate, as described above, to maintain the pressure (vacuum) in conduit 28 at the level requested by the surgeon by means of the signal carried at 50.

When the system is operated in a flow-controlled mode, pump 12 must be operated at a flow rate equal to the flow rate through conduit 28, which is requested by the surgeon, plus any additional flow of gas through the conduit 32. In this regard, the variable flow resistor 20 is normally maintained at its maximum resistance (minimum flow). However, under most circumstances, some small flow of gas should be permitted, so that the flow director 16 remains open and the pressure (vacuum) sensor 18 remains in communication with the conduit 28. Further, the maximum resistance of the variable flow resistor 20 should be predetermined so that the rate of flow of gas through the conduit 32 may be calculated from the pressures at the conduits 42 (which must be known or assumed) and 40 (which is sensed by the pressure sensor 18). As described above, the flow rate so calculated must be added to the flow rate requested by the surgeon to determine the flow rate at which the pump 12 should be operated. If desired, a maximum vacuum limit may be set by means of the electrical signal as carried at 50. If the electrical signal as carried at 48 from the pressure (vacuum) sensor 18 exceeds this limit, the control circuit 24 will act upon the variable flow resistor 20 to reduce its resistance and increase the flow of gas through the variable flow resistor 20, such that the pressure (vacuum) is maintained at the established limit.

In the event that the flow rate through the conduit 28 temporarily exceeds the flow rate through the pump 12, as might occur with a failure of the pump 12, the flow director 16 acts to prevent the flow of aspirated liquid from the conduit 32 into the conduit 36. This is required to protect the pressure (vacuum) sensor 18 and the variable flow resistor 20 from contamination.

Upon completion of the surgical procedure, the conduits 28, 30, 32, and 34, and the collector 14, and the flow director 16 are disposed of, as they are not intended for re-use.

It is to be understood that the invention is not confined to the particular construction and arrangement of parts herein illustrated and described, but embraces such modified forms thereof as come within the scope of the following claims.

What is claimed is:

1. A surgical aspiration system comprising:
   (a) a first conduit having a first end and a second end, the first end and the second end being in fluid communication and the first end communicating with the surgical site from which fluid is to be aspirated;
   (b) a second conduit having a first end and a second end, the first end of the second conduit and the second end of the second conduit being in fluid communication, the second end of the first conduit and the first end of the second conduit meeting at a juncture which permits fluid communication therethrough;
   (c) a collector which is in fluid communication with the second end of the second conduit, the collector receiving aspirated fluid;
   (d) a pump which induces flow of aspirated fluid through the second conduit, and into the collector;
   (e) a third conduit having a first end and a second end, the first end of the third conduit and the second end of the third conduit being in fluid communication, the first end of the third conduit meeting at the juncture such that it is in fluid communication with the second end of the first conduit and the first end of the second conduit;
   (f) a flow director having an input and an output, the output being located at the second end of the third conduit and being in fluid communication with the second end of the third conduit, the flow director permitting flow of gas into the third conduit and preventing the flow of liquid to the input of the flow director.
   (g) a fourth conduit having a first end and a second end, the first end of the fourth conduit and the second end of the fourth conduit being in fluid communication, the second end of the fourth conduit being in fluid communication with the input of the flow director;
   (h) a proportional valve having a first port and a second port, the first port being in fluid communication with the first end of the fourth conduit;
   (i) a gas source being in fluid communication with the second port of the proportional valve;
   (j) a pressure sensor which is in fluid communication with the fourth conduit and which produces a signal proportional to the pressure in the fourth conduit;
   (k) operator input means which produce a signal proportional to the desired pressure level; and
   (l) control means which control the proportional valve to maintain the pressure in the fourth conduit as indicated by the signal produced by the pressure sensor approximately equal to the desired pressure level as indicated by the signal produced by the operator input means.

2. The system of claim 1 wherein the flow director is a one-way valve.

3. The system of claim 1 wherein the flow director is a hydrophobic membrane.

4. The system of claim 1 wherein the pump is a peristaltic pump.

5. The system of claim 1 wherein the gas source is the atmosphere.

6. The system of claim 1 wherein the fourth conduit further communicates with an orifice disposed between the fourth conduit and the gas source.

7. A surgical aspiration system comprising:
   a conduit which communicates with a surgical site from which fluid is to be aspirated;
   a first portion of connective plumbing disposed in fluid communication with the conduit;
   a second portion of connective plumbing disposed in fluid communication with the first section;
   a flow director connecting in fluid flowing relation the first and second portions of connective plumbing, and wherein the flow director permits fluid movement in the direction from the second portion to the first portion;
   a collector for receiving aspirated fluid from the conduit and which is connected in fluid flowing communication with the first portion of the plumbing;
   a pump for inducing the flow of aspirated fluid from the conduit to the collector, and which is disposed in fluid communication with the first portion of the connective plumbing;
   a pressure sensor disposed in fluid flowing relation relative to the second portion of the connective plumbing;
   a variable flow resistor disposed in fluid flowing relation relative to the second portion of the connective plumbing;
   a gas source connected in fluid flowing relation relative to the variable flow resistor to provide a known pressure against which pressure in the remainder of the connective plumbing is compared to establish a pressure differential;
   operator input means which produces a signal proportional to a user selected pressure level; and
   control means for adjusting the variable flow resistor and the pump for use in first and second modes of operation, and wherein the control means is disposed in signal receiving relation relative to the pressure sensor, and wherein in the first mode of operation, the variable flow resistor is adjusted to maintain a preselected pressure conveyed by the conduit which is approximately equal to the preselected pressure level as indicated by the operator input means, and in the second mode of operation the control means adjusting the pump to maintain a predetermined flow according to the pressure differential as established in the connective plumbing.

8. A surgical aspiration system as claimed in claim 7, and wherein the flow director is a one-way valve.

9. A surgical aspiration system as claimed in claim 7, and wherein the flow director is a hydrophobic membrane.

10. A surgical aspiration system as claimed in claim 7, and wherein the pump is a peristaltic pump.

11. A surgical aspiration system as claimed in claim 7 and wherein the gas source is the atmosphere.

12. A surgical aspiration system as claimed in claim 7, and wherein the first portion of the plumbing is detachable from the second portion.

* * * * *